US006888020B2

United States Patent
Kim et al.

(10) Patent No.: US 6,888,020 B2
(45) Date of Patent: May 3, 2005

(54) WATER-SOLUBLE DITHIOESTERS AND METHOD FOR POLYMERIZATION THEREOF

(75) Inventors: Hee-Jung Kim, Daejeon (KR); Dong-Ryul Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 10/472,573

(22) PCT Filed: Jan. 15, 2003

(86) PCT No.: PCT/KR03/00082
§ 371 (c)(1),
(2), (4) Date: Oct. 27, 2003

(87) PCT Pub. No.: WO03/062280
PCT Pub. Date: Jul. 31, 2003

(65) Prior Publication Data
US 2004/0138492 A1 Jul. 15, 2004

(30) Foreign Application Priority Data
Jan. 25, 2002 (KR) .............................. 10-2002-0004565
Jan. 9, 2003 (KR) .............................. 10-2003-0001407

(51) Int. Cl.$^7$ .......................... C07F 9/02; C07C 237/20
(52) U.S. Cl. ...................................... 558/181; 558/235
(58) Field of Search .............................. 558/181, 235, 558/230, 231, 249

(56) References Cited

U.S. PATENT DOCUMENTS 4,581,429 A  4/1986  Solomon et al. ............ 526/220

FOREIGN PATENT DOCUMENTS

| WO | WO 989/01478 | 1/1998 |
| WO | WO 99/05099 | 2/1999 |
| WO | WO 99/31144 | 6/1999 |

OTHER PUBLICATIONS

CA:138:221893 abs of JACS by Coote et al 125(6) pp 1490–1491 2003.*
CA:138:24786 abs of Journal of Organic Chem. by Alberti et al 67(22) pp 7911–7914 2002.*

"Reversible Addition–Fragmentation Chain–Transfer Polymerization for the Synthesis of Poly(4–acetoxystryrene) and Poly(4–acetoxystyrene)–block–polystyrene by Bulk, Solution and Emulsion Techniques"; Authors: Subbareddy Kanagasabapathy, Arumugam Sudalai and Brian C. Benicewicz; Macromol. Rapid Commun., vol. 22, No. 13; 2001; pp. 1076–1080.

"A Novel Synthesis of Functional Dithioesters, Dithiocarbamates, Xanthates and Trithiocarbonates"; Authors: San H. Thang, (Bill) Y.K. Chong, Roshan T. A. Mayadunne, Graeme Moad and Ezio Rizzardo; Pergamon; Tetrahedron Letters 40; 1999; pp. 2435–2438.

"Short Communications"; Authors: P. Cairon, B. Labiad and D. Villemin; Eur. Polym. J., vol. 24, No. 7; 1988; pp. 697–698.

"Narrow Molecular Weight Resins by a Free–Radical Polymerization Process"; Authors: Michael K. Georges, Richard P.N. Veregin, Peter M. Kazmaier and Gordon K. Hamer; Macromolecules, vol. 26, No. 11; American Chemical Society; 1993; pp. 2987–2988.

"Living Free–Radical Polymerization by Reversible Addition–Fragmentation Chain Transfer: The RAFT Process"; Authors: John Chiefari, et al.; Macromolecules, vol. 31, No. 16; American Chemical Society; 1998; pp. 5559–5562.

"A New Practical Synthesis of Tertiary S–Alkyl Dithiocarbonates and Related Derivatives"; Authors: Ghenwa Bouhadir, Nicolas Legrand, Beatrice Quiclet–Sire and Samir Z. Zard; Pergamon; Tetrahedron Letters 40; 1999; pp. 277–280.

PCT International Search Report; International application No. PCT/KR03/00082; International filing date of Jan. 15, 2003; Mailing date of Aug. 12, 2003.

* cited by examiner

*Primary Examiner*—Johann Richter
*Assistant Examiner*—Chukwuma Nwaonicha
(74) *Attorney, Agent, or Firm*—Cantor Colburn LLP

(57) ABSTRACT

Disclosed are water soluble dithioesters capable of acting as chain transfer agents in preparing a vinyl-based polymer to control molecular weight and molecular weight distribution thereof as well as being capable of living polymerization even in an aqueous solution, and a method for polymerization thereof.

3 Claims, No Drawings

WATER-SOLUBLE DITHIOESTERS AND METHOD FOR POLYMERIZATION THEREOF

CROSS REFERENCE TO RELATED APPLICATION

BACKGROUND OF THE INVENTION (a) Field of the Invention

The present invention relates to water soluble dithioesters capable of acting as chain transfer agents in preparing a vinyl-based polymer to control the molecular weight and the molecular weight distribution thereof, as well as being capable of living polymerization even in an aqueous solution, and a method for polymerization thereof.

(b) Description of the Related Art

A living polymerization process has characteristics of a living polymerization system in that it is capable of controlling a resultant polymer to a higher level, and particularly of controlling the resultant polymer within a narrow molecular weight distribution and controlling the length and the composition of at least one monomer by adjusting the reaction condition and the reaction conversion rate.

Solomon et al. first introduced living free-radical polymerization by using a nitroxide-based stable radical in order to control a polymerization reaction, in U.S. Pat. No. 4,581, 429. Based on this approach, Georges et al. disclosed living radical polymerization in which the resultant polymer-has an increased average molecular weight as the yield increases when the polymerization is carried out at a higher temperature, so that the molecular weight is narrowly distributed (Macromolecules 26, 2987 (1993)). Nonetheless, this polymerization has problems in that the available monomer is limited and a condition of high temperature, is required. Further, Matyjasewski et al. disclose a living radical polymerization system in which atoms are transferred by using a metal complex, which is successfully practiced with acryl- and styrene-based monomers. Even so, commercial utilization of this polymerization system is limited since residual metals are produced. Therefore, introduction of a novel polymerization process is still required in order to overcome the above-mentioned problems.

Moad et al. also disclosed successful living polymerization by using a dithioester-based organic material, in Macromolecules 31, 5559 (1998) and WO 98/01478. This method, however, has problems in that the yield is excessively low since dithiobenzoic salt/acid is difficult to react with a halide compound and it is difficult to use various halogen compounds.

Unlike the above synthetic processes, WO 99/05099, WO 99/31144, Tetrahedron letters 40, 2435–2438, 1999, and Tetrahedron letters 40, 277–280, 1999 disclose a synthetic method of various dithioesters by using a radical termination reaction between dithiobenzoyl disulfide and an azo-based initiator, and living polymerization using the obtained compound.

Although the diverse approaches involve dithioesters, provision of water soluble dithioesters is still demanded.

SUMMARY OF THE INVENTION

It is an object of the present invention to provide water soluble dithioesters capable of acting as chain transfer agents in preparing a vinyl-based polymer to control molecular weight and molecular weight distribution thereof, as well as being capable of living polymerization even in an aqueous solution.

It is another object to provide a method for polymerization of said water-soluble dithioesters.

These and other objects may be achieved by water soluble dithioesters represented by the following Chemical Formula 1:

[Chemical Formula 1]

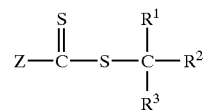

In the Chemical Formula 1,

Z is a hydrogen, a chlorine, an alkyl, an aryl, an alkylthio, an alkoxycarbonyl, an aryoxycarbonyl (—COOR"), an carboxy (—COOH), an acyloxy (—O$_2$CR"), a cabamoyl (—CONR"), a cyano (—CN), a dialkyl-phosphonato, a diaryl-phosphonato (—P(=O)OR"$_2$), a dialkyl-phosphinato, a diaryl-phosphinato (—P(=O)R"$_2$) which contains or does not contain substitutents, R" is $C_{1-18}$ alkyl, $C_{2-18}$ alkenyl, aryl, heterocyclyl, aralkyl, or alkylaryl which contains or does not contain substitutents are selected from the group of epoxy, alkoxycarbonyl, aryloxycarbonyl, isocyanto, cyano, siyl, hoal, and dialkylamino, $R^1$ is $C_{1-18}$ alkyl, $C_{2-18}$ alkenyl, aryl, heterocyclyl, aralkyl, or alkylaryl which contains or does not contain substitutents are selected from the group of hydrogen, ester, keto, amide, ether, thio, hydroxy, cyano, siyl, haloyl, and dialkylamino, and $R^2$, and $R^3$ are independently $C_{1-18}$ alkyl, $C_{2-18}$ alkenyl, aryl, heterocyclyl, aralkyl, or alkylaryl which contains or does not contain substitutents are selected from the group of ester, keto, amide, ether, thio, hydroxy, cyano, siyl, haloyl, and dialkylamino, and at least one of $R^2$, and $R^3$ contains an ammonium salt represented by the Chemical Formula 2 having a cationic substitutent at its end or a hetero ring salt which contains or does not contain substitutents represent by the Chemical Formula 3:

[Chemical Formula 2]

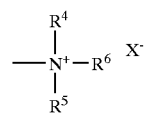

In the Chemical Formula 2, $R^4$, $R^5$, and $R^6$ are independently an alkyl which contains branched, normal saturated or unsaturated, alkyl which contain aryl substitutent, alkoxyalkyl, cyanoalkyl, or hydroxyalkyl, X is a halide or a sulfate having a functional group capable of forming a salt or an anion,

[Chemical Formula 3]

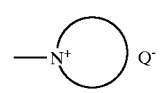

In the Chemical Formula 3,

The hetero ring is ring compound having 5,6-square shape, and can be contained independently alkyl, or alkene, nitrogen can be 1 to 3, and preferably the third nitrogen chemical, Q is a halide or a sulfate having a functional group capable of forming a salt or an anion.

The present invention further includes a method for polymerization of said water-soluble dithioesters represented by Chemical Formula 1, comprising the steps of:

a) providing a disulfide compound represented by the following Chemical Formula 4: and b) reacting the disulfide compound obtained from the step a) in the presence of an initiator and a solvent:

[Chemical Formula 4]

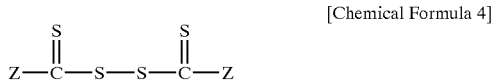

In the Chemical Formula 4,

Z is a hydrogen, a chlorine, an alkyl, an aryl, an alkylthio, an alkoxycarbonyl, an aryoxycarbonyl (—COOR"), an carboxy (—COOH), an acyloxy (—O$_2$CR"), a cabamoyl (—CONR"), a cyano (—CN), a dialkyl-phosphonato, a diaryl-phosphonato (—P(=O)OR"$_2$), a dialkyl-phosphinato, a diaryl-phosphinato (—P(=O)R"$_2$) which contains or does not contain substitutents, R" is $C_{1-18}$ alkyl, $C_{2-18}$ alkenyl, aryl, heterocyclyl, aralkyl, or alkylaryl which contains or does not contain substitutents are selected from the group of epoxy, alkoxycarbonyl, aryloxycarbonyl, isocyanto, cyano, siyl, hoal, and dialkylamino.

DETAILED DESCRIPTION OF THE PREFERRED EMBODIMENTS

In the following detailed description, only the preferred embodiment of the invention has been shown and described, simply by way of illustration of the best mode contemplated by the inventors of carrying out the invention. As will be realized, the invention is capable of modification in various obvious respects, all without departing from the invention. Accordingly, the description is to be regarded as illustrative in nature, and not restrictive.

The present inventors studied water soluble dithioesters capable of acting as chain transfer agents in preparing a vinyl-based polymer to control molecular weight and molecular weight distribution thereof, and as a result, they succeeded in polymerizing water soluble dithioesters in the presence of an initiator and a solvent. The present invention can thereby provide water soluble dithioesters capable of acting as chain transfer agents in preparing a vinyl-based polymer to control the molecular weight and the molecular weight distribution thereof, as well as of being capable of living polymerization even in an aqueous solution.

According to the present invention, water soluble dithioesters represented by Chemical Formula 1 are characterized in that they are prepared by providing a disulfide compound represented by Chemical Formula 4 and by subsequently polymerizing the compound in the presence of an initiator and a solvent.

In Chemical Formula 1, the heteroaromatic group may preferably have at least one hetero atom such as O, N, and S, and the examples thereof include, but are not limited to, pyrrolidine, indole, imidazole, carbazole, benzimidazole, and piperidine.

The representative examples of water soluble dithioesters represented by Chemical Formula 1 are as shown in the following Chemical Formulas 1a~1d:

[Chemical Formula 1a: 4-cyano-4-(thiobenzylthio) pentanoic trimethylammonium chloro ethyl ester]

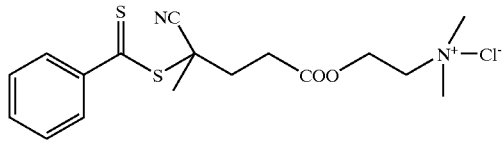

[Chemical Formula 1b: 4-cyano-4-(thiobenzylthio) pentanoic diethyl benzylammonium bromo ethyl ester]

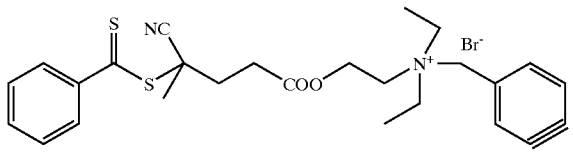

[Chemical Formula 1c: 4-cyano-4-(thiobenzylthio) pentanoic diisopropyl methylammonium chloro ethyl ester]

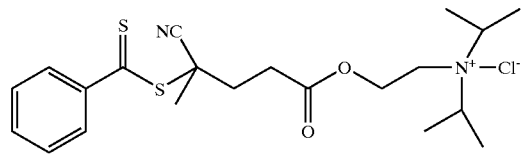

[Chemical Formula 1d: 4-cyano-4-(dithiopyrrole) pentanoic pyridum bromo ethyl ester]

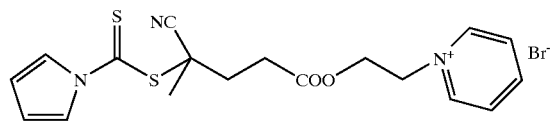

The examples of water soluble dithioesters represented by Chemical Formula 1 may be prepared by following a process comprising the steps of:

a) adding an iodine aqueous solution to an aqueous solution of sodium salt of dithiobenzoic acid and oxidizing it to provide dithiobenzoyl disulfide represented by Chemical Formula 4; and b) reacting the dithiobenzoyl disulfide in the presence of an initiator and a solvent.

The initiator used in the b) step may be any initiator as long as it has a suitable half-life period in relation to the reacting temperature. It also includes one that is thermally introduced and one that is photo-reactively introduced. The preferable initiator is an azo-based compound, and it is more preferably a certain initiator in which the substitute does not produce a side reaction with a dithiobenzyl functional group. Any initiator having a primary or secondary amine is unfavorable due to the generation of a side reaction with the dithiobenzyl functional group to form dithioamide.

The suitable solvent for the reaction between dithiobenzoyl disulfide and the initiator in step b) is any solvent having as small a chain transfer constant against a radical as is theoretically possible.

The examples of solvents include, but are not limited to, water, alcohol, an ether, an ester, a ketone, an amide, an aliphatic hydrocarbon, or an aromatic hydrocarbon, and specifically water, methylisobutylcarbinol, methyl alcohol, ethyl alcohol, isopropyl alcohol, propyl alcohol, butyl alcohol, hexyl alcohol, heptyl alcohol, octyl alcohol, nonyl alcohol, 3-methyl butyl alcohol, propylene glycol, 3-methoxy butyl alcohol, 3-methyl-3-methoxy butyl alcohol, propyleneglycol monomethylether, propyleneglycol monopropylether, propyleneglycol monobutylether, dipropyleneglycol monomethylether, dipropyleneglycol monopropylether, dipropyleneglycol monobutylether, tripropyleneglycol monomethylether, tripropyleneglycol monopropylether, tripropyleneglycol monobutylether, propyleneglycol dimethylether, propyleneglycol diethylether, dipropyleneglycol dimethylether, tripropyleneglycol dimethylether, 3,5,5-trimethyl-1-hexanol, 2-ethyl-1-hexanol, cyclohexanol, benzyl alcohol, acetone, methylethylketone, methylisobutylketone, methyl isoamylketone, acetophenone, propiophenone, benzophenone, cyclohexanone, isophorone, pyrrolidone, N-methylpyrrolidone, dimethylformamide, dimethylacetamide, dimethylsulfoxide, sulfolane, methyl acetate, ethyl acetate, butyl acetate, isobutyl acetate, amyl acetate, 3-methoxybutylacetate, 3-methyl-3-methoxybutylacetate, methyl lactate, ethyl lactate, butyl lactate, methyl-3-methoxypropionate, ethyl-3-ethoxypropionate, 2-ethylhexylacetate, cyclohexylacetate, benzylacetate, methylpropionate, ethylpropionate, butylpropionate, benzylpropionate, methylbenzoate, ethylbenzoate, propylbenzoate, isoamylbenzoate, benzylbenzoate, diethylether, dipropylether, dibutylether, diphenylether, benzylmethylether, benzylethylether, anisole, phenetole, butylphenylether, methoxyltoluene, tetrahydrofurane, dibenzylether, acetonitrile, γ-butyrolactone, propylene carbonate, propyleneglycol monomethyletheracetate, propyleneglycol monomethyletherpropionate, dipropyleneglycol monomethyletheracetate, propyleneglycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, methyl cinnamate, ethyl cinnamate, benzene, xylene, toluene, tetralin, decalin, limonene, methyl cellosolve, ethyl cellosolve, 1,4-dioxane, chloroform, methylenechloride, 1,2-dichloroethane, 1,1,1-trichloroethane, 1,1,2-trichloroethane, 1,1,2-trichloroethene, hexane, heptane, octane, cyclohexane, cyclohexanone, ethyl cellosolveacetate, methyl cellosoveacetate, N,N-dimethylformamide, methyl α-methoxyisobutyrate, ethyl α-methoxyisobutyrate, methyl α-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate, and a mixture thereof are preferred.

The water soluble dithioesters represented by Chemical Formula 1 can be applied as chain transfer agents to control molecular weight and molecular weight distribution in preparing a vinyl polymer as well as being capable of living polymerization in an aqueous solution.

The following Examples further illustrate the present invention in detail, but are not to be construed to limit the scope thereof.

EXAMPLES

Example 1

Preparation of Dithiobenzoyl Disulfide 100 ml of a sodium salt solution of dithiobenzoic acid (0.15 mol) were added by drops to an 80 not iodine aqueous solution (0.1 mol) over 1 hour. After completing the reaction, the obtained product was dissolved in an organic solvent of tetrahydrofurane (THF) and washed with distillated water twice and dried over magnesium sulfate ($MgSO_4$). The organic solvent was removed by vacuum evaporation. It was then recrystalized in ethanol to obtain dithiobenzoyl disulfide.

Preparation of (4-cyano-4-(thiobenzylthio)pentanoic trimethylammonium chloro ethyl ester (Compound of Chemical Formula 1a)

43 g of the resultant dithiobenzoyl disulfides (142 mmol) and 51.68 g 4,4'-azobis(4-cyanovoleric acid) (manufactured by WACO) were dissolved in 800 g of ethyl acetate solvent, and refluxed under a nitrogen atmosphere for 18 hours. After completing the reaction, the organic fraction was distillated in vacuum and purified using a column to obtain 25 g of 4-cyano-4-(thiobenzylthio) pentanoic acid (63% yield).

25 g of 4-cyano-4-(thiobenzylthio) pentanoic acid (89.6 mmol) were dissolved in 100 g of tetrahydrofurane anhydride. Under a nitrogen atmosphere, 15.726 g of 10-hydroxy benzotriazole (0.116 mol) were added thereto and stirred for 30 minutes. 22.72 g ethyldimethylaminocarboimide (0.116 mol) were added and stirred for 15 minutes, followed by the addition of 11.98 g of dimethylaminoethanol (0.134 mol) and stirring at room temperature for 6 hours. After completing the reaction, the resultant was extracted with water and diethyl ether and dried over magnesium sulfate. The organic solvent was vacuum distillated. It was purified with a column to obtain 21.95 g of 4-cyano-4-(thiobenzylthio) pentanoic dimethylamino ethyl ester (70% yield).

22 g of the obtained 4-cyano-4-(thiobenzylthio)pentanoic dimethylamino ethyl ester (62.7 mmol) were poured into a reactor, then 125 ml of methyl chloride (1.0 M diethylether solution, 0.125 mol) were added thereto, and it was stirred at room temperature for 16 hours. After completing the reaction, diethyl ether was added to induce precipitation, then the resultant was filtered to obtain 20.57 g of 4-cyano-4-(thiobenzylthio)pentanoic trimethylammonium chloro ethyl ester (85% yield).

$^1$H-NMR($CDCl_3$) δ(ppm) 2.01(s, 3H, $CH_3$)2.2–2.7(m, 4H, $CH_2CH_2$), 3.33(s, 9H, $CH_3$), 3.866(t, 2H, $CH_2$), 4.31 (t, 2H, COO—$CH_2$) 7.27 (m, 1H, para-ArH), 7.31(m, 1H, meta-ArH) 7.97(m. 1H, ortho-ArH)

Example 2

Preparation of (4-cyano-4-(thiobenzylthio)pentanoic diethyl benzylammonium bromo ethyl ester (Compound of Chemical Formula 1b)

23.14 g of dithiobenzoyl disulfide (75.62 mmol) from Example 1 and 27.524 g of 4,4-azobis(4-cyanovoleric acid) (manufactured by WACO) were dissolved in 400 g of ethyl acetate solvent, and refluxed for 18 hours under a nitrogen atmosphere. After completing the reaction, the organic fraction was distillated under vacuum and purified using a column to obtain 16.9 g of 4-cyano-4-(thiobenzylthio) pentanoic acid (64% yield).

16.9 g of the obtained 4-cyano-4-(thiobenzylthio) pentanoic acid (48.4 mmol) were dissolved in 100 g of tetrahydrofurane anhydride. Under a nitrogen atmosphere, 8.496 g of 10-hydroxy benzotriazole (0.0629 mol) were added thereto, and stirred for 30 minutes. 12.26 g of ethyldimethylaminocarboimide (0.0629 mol) were added and stirred for 15 minutes, followed by addition of 11.47 g of diethylaminoethanol (0.0981 mol). The stirring was continued at room temperature for 12 hours. After completing the reaction, the resultant was extracted with water and diethyl ether, and dried over magnesium sulfate. The organic solvent was distillated in a vacuum, then purified with a column to obtain 12.8 g of 4-cyano-4-(thiobenzylthio)pentanoic diethylamino ethyl ester (70% yield).

12.8 g of the obtained 4-cyano-4-(thiobenzylthio) pentanoic diethylamino ethyl ester (33.8 mmol) were poured into a reactor, followed by 60.2 g benzyl bromide, then the solution was stirred at room temperature for 6 hours. After completing the reaction, diethyl ether was added to induce precipitation, and unreacted iode methane was removed to obtain 15.58 g of 4-cyano-4-(thiobenzylthio)pentanoic diethylbenzylammonium bromo ethyl ester (84% yield).

$^1$H-NMR(CDCl$_3$) δ(ppm) 1.14(t, 6H, CH$_3$) 1.98(s, 3H, CH$_3$) 2.24–2.66(m, 4H, CH$_2$CH$_2$), 3.2–3.4(m, 4H, N—CH$_2$), 3.8–4.0(t, 2H, CH$_2$), 4.31(t, 2H, COO—CH$_2$), 4.6–4.8(m, 2H, Pyr-CH$_2$—N), 6.9–7.5(m, 5H, Pyr), 7.27 (m, 1H, para-ArH), 7.31 (m, 1H, meta-ArH) 7.97(m, 1H, ortho-ArH)

Example 3

Preparation of (4-cyano-4-(thiobenzylthio)pentanoic diisopropyl methylammonium chloro ethyl ester (compound of Chemical Formula 1c)

18.25 g of dithiobenzoyl disulfide (59.65 mmol) from Example 1 and 21.7 g of 4,4-azobis(4-cyanovoleric acid) (manufactured by WACO) were dissolved in 350 g of ethyl acetate solvent, and the solution was refluxed for 18 hours under a nitrogen atmosphere. After completing the reaction, the organic fraction was distillated under vacuum and purified using a column to obtain 12.7 g of 4-cyano-4-(thiobenzylthio) pentanoic acid (61% yield).

12.7 g of the obtained 4-cyano-4-(thiobenzylthio) pentanoic acid (36.39 mmol) were dissolved in 60 g tetrahydrofurane anhydride. Under a nitrogen atmosphere, 6.36 g of 10-hydroxy benzotriazole (0.0473 mol) were added thereto and stirred for 30 minutes. 9.22 g of ethyldimethylaminocarboimide (0.0473 mol) were added and stirred for. 15 minutes, followed by the addition of 7.9 g of diisopropylene diamine (0.0546213 mol) and stirring at room temperature for an additional 12 hours. After completing the reaction, the resultant was extracted with water and diethyl ether, and dried over magnesium sulfate. The organic solvent was distillated under vacuum, and purified with a column to obtain 10.35 g of 4-cyano-4-(thiobenzylthio)pentanoic diisopropyl amino ethyl ester (70% yield).

10.35 g of the obtained 4-cyano-4-(thiobenzylthio) pentanoic diisopropylene amino ethyl ester (25.47 mmol) were poured into a reactor, followed by 76 ml of methyl chloride (1.0 M diethyl ether solution, 76 mol). The solution was stirred at room temperature for 16 hours. After completing the reaction, diethyl ether was added to induce precipitation, and the resultant was filtered to obtain 9.36 g of 4-cyano-4-(thiobenzylthio)pentanoic diisopropyl methylammonium chloro ethyl ester (83% yield).

Example 4

Preparation of (4-cyano-4-(dithiopyrrole)pentanoic pyridum bromo ethyl ester compound of Chemical Formula 1d)

31.4 g pyrrol-N-thiocarbonyl disulfides (0.11 mol) and 40.04 g 4,4'-azobis (4-cyanovoleric acid) (manufactured by WACO) were dissolved in 700 g of ethyl acetate solvent, and the solution was refluxed for 18 hours under a nitrogen atmosphere and dissolved in 100 g of dioxine. Under a nitrogen atmosphere at 100° C., 303 g of an initiator of 4,4-azobis-(4-cyanovoleric acid) were added by drops over 2 hours. After completing the reaction, the organic fraction was distillated under vacuum and purified using a column to obtain 17.42 g of 4-cyano-4-(thiobenzylthio) pentanoic acid (59% yield).

17.42 g of the obtained 4-cyano-4-(thioimidazoyl) pentanoic acid (0.065 mol) were dissolved in 100 g tetrahydrofurane anhydride, and 11.4 g of 10-hydroxy benzotriazole (0.0845 mol) were added thereto under a nitrogen atmosphere and the solution was stirred for 30 minutes. 16.47 g of ethyldimethylaminocarboimide (0.0845 mol) were added thereto, followed by stirring for 15 minutes, then 12.18 g of 2-bromoethanol (0.0975 mol) were added and stirring was continued at room temperature for 12 hours. After completing the reaction, the resultant was extracted with water and diethyl ether, and dried over magnesium sulfate, and the organic solvent was distillated under a vacuum. The remainder was purified with a column to obtain 12.19 g of 4-cyano-4-(dithioimidazoyl) pentanoic 2-bromo ethyl ester (50% yield).

12.19 g of the obtained 4-cyano-4-(thiobenzylthio) pentanoic 2-bromo ethyl ester (32.5 mmol) were poured into a reactor, then 11.53 g of pyridine (0.162 mol) were added thereto and the solution was stirred at room temperature for 36 hours. After completing the reaction, diethyl ether was added to induce precipitation and the unreacted pyridine was removed to obtain 11.62 g of 4-cyano-4-(dithiopyrrole) pentanoic pyridum bromo ethyl ester (80% yield).

$^1$H-NMR(CDCl$_3$) δ(ppm) 1.93(s, 3H, CH$_3$), 2.2–2.4(m, 2H, CH$_2$), 2.7(t, 2H, COCH$_2$), 3.89(t, 2H, COO—CH$_2$), 4.24(m, 2H, ortho-PyrH), 6.24(m, 2H, meta-PyrH), 6.48(m, 2H, ortho-pyrolleH), 6.78(m, 2H, meta-pyrolleH), 6.99(m, 1H, para-PyrH)

As stated above, the water soluble diithio esters according to the present invention can act as a chain transfer agent in preparing a vinyl-based polymer to control the molecular weight and molecular weight distribution thereof, as well as being capable of living polymerization even in an aqueous solution.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A water soluble dithioester compound represented by the following Chemical Formula 1:

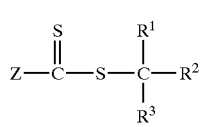

[Chemical Formula 1]

in the Chemical Formula 1,

Z is a hydrogen, a chlorine; or an alkyl, an aryl, an alkylthio, an alkoxycarbonyl, an aryoxycarbonyl (—COOR"), an carboxy (—COOH), an acyloxy (—O$_2$CR"), a cabamoyl (—CONR"), a cyano (—CN), a dialkyl-phosphonato, a diaryl-phosphonato (—P(=O)OR"$_2$), a dialkyl-phosphinato, or a diaryl-phosphinato (—P(=O)R"$_2$) unsubstituted or substituted which substitutents, R" is $C_{1-18}$ alkyl, $C_{2-18}$ alkenyl, aryl, heterocyclyl, aralkyl, or alkylaryl unsubstituted or substituted with a substitutent selected from the group consisting of epoxy, alkoxycarbonyl, aryloxycarbonyl, isocyanto, cyano, silyl, halo, and dialkylamino, $R^1$ is $C_{1-18}$ alkyl, $C_{2-18}$ alkenyl, aryl, heterocyclyl, aralkyl, or alkylaryl unsubstituted or substituted with a substitutent selected from the group consisting of hydrogen, ester, keto, amide, ether, thio, hydroxy, cyano, silyl, halo, and dialkylamino, and $R^2$ and $R^3$ are independently $C_{1-18}$ alkyl, $C_{2-18}$ alkenyl, aryl, heterocyclyl, aralkyl, or alkylaryl unsubstituted or substituted with a substitutent selected from the group consisting of ester, keto, amide, ether, thio, hydroxy, cyano, silyl, halo, and dialkylamino, and at least one of $R^2$ and $R^3$ contains an ammonium salt represented by the Chemical Formula 2 having a cationic substitutent at its end or a hetero ring salt unsubstituted or substituted with substitutents represent by the Chemical Formula 3:

[Chemical Formula 2]

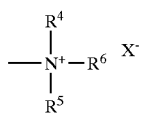

in the Chemical Formula 2, $R^4$, $R^5$, and $R^6$ are independently an alkyl which contains branched, normal saturated or unsaturated, alkyl which contain aryl substitutent, alkoxyalkyl, cyanoalkyl, or hydroxyalkyl, X is a halide or a sulfate,

[Chemical Formula 3]

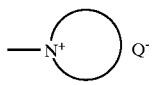

in the Chemical Formula 3, a hetero ring of hetero ring salt is heterocyclic moiety having 5 or 6 membered rings, and can contain independently alkyl, or alkene, Q is a halide or a sulfate.

2. The water soluble dithioester compound according to claim 1, wherein the water soluble dithioester compound is selected from the group consisting of compounds represented by the following Chemical Formula 1a, compounds represented by the following Chemical Formula 1b, compounds represented by the following Chemical Formula 1c, and compounds represented by the following Chemical Formula 1d:

[Chemical Formula 1a]

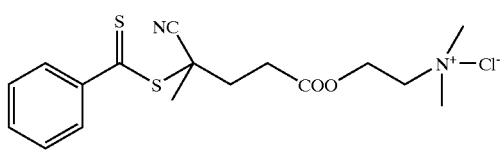

[Chemical Formula 1b]

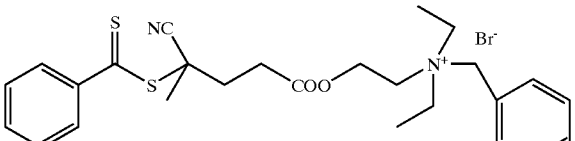

[Chemical Formula 1c]

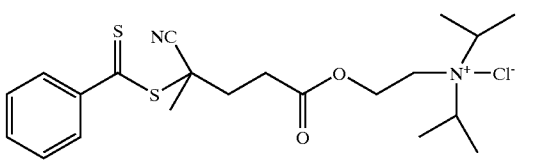

[Chemical Formula 1d]

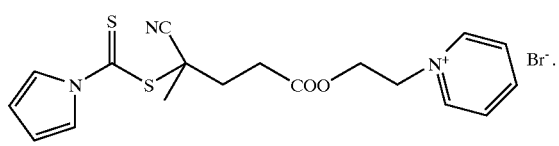

3. A chain transfer agent for preparing a vinyl-based polymer comprising a water soluble dithioester compound represented by the following Chemical Formula 1:

[Chemical Formula 1]

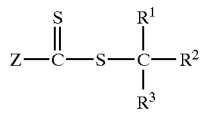

in the Chemical Formula 1,

Z is a hydrogen, a chlorine; or an alkyl, an aryl, an alkylthio, an alkoxycarbonyl, an aryoxycarbonyl (—COOR"), an carboxy (—COOH), an acyloxy (—O$_2$CR"), a cabamoyl (—CONR"), a cyano (—CN), a dialkyl-phosphonato, a diaryl-phosphonato (—P(=O)OR"$_2$), a dialkyl-phosphinato, or a diaryl-phosphinato (—P(=O)R"$_2$) unsubstituted or substituted which substitutents, R" is $C_{1-18}$ alkyl, $C_{2-18}$ alkenyl, aryl, heterocyclyl, aralkyl, or alkylaryl unsubstituted or substituted with a substitutent selected from the group consisting of epoxy, alkoxycarbonyl, aryloxycarbonyl, isocyanto, cyano, silyl, halo, and dialkylamino, $R^1$ is $C_{1-18}$ alkyl, $C_{2-18}$ alkenyl, aryl, heterocyclyl, aralkyl, or alkylaryl unsubstituted or substituted with a substitutent selected from the group consisting of hydrogen, ester, keto, amide, ether, thio, hydroxy, cyano, silyl, halo, and dialkylamino, and $R^2$ and $R^3$ are independently $C_{1-18}$ alkyl, $C_{2-18}$ alkenyl, aryl, heterocyclyl, aralkyl, or alkylaryl unsubstituted or substituted with a substitutent selected from the group consisting of ester, keto, amide, ether, thio, hydroxy, cyano, silyl, halo, and dialkylamino, and at least one of $R^2$ and $R^3$ contains an ammonium salt represented by the Chemical Formula 2 having a cationic substitutent at its end or a hetero ring salt unsubstituted or substituted with substitutents represent by the Chemical Formula 3:

[Chemical Formula 2]

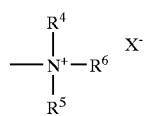

in the Chemical Formula 2, $R^4$, $R^5$, and $R^6$ are independently an alkyl which contains branched, normal saturated or unsaturated, alkyl which contain aryl substitutent, alkoxyalkyl, cyanoalkyl, or hydroxyalkyl, X is a halide or a sulfate,

[Chemical Formula 3]

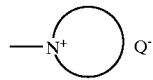

in the Chemical Formula 3, a hetero ring of the hetero ring salt is heterocyclic moiety having 5 or 6 membered rings, and can contain independently alkyl, or alkene, Q is a halide or a sulfate.

* * * * *